United States Patent [19]

Benthin et al.

[11] Patent Number: 4,660,564

[45] Date of Patent: Apr. 28, 1987

[54] APPARATUS FOR MEASURING PULSETILE PART-STRUCTURES WITHIN A LIVING BODY

[75] Inventors: Morten Benthin; Philip I. Dahl, both of Lund; Gerhard M. Gennser, Malmo; Kjell O. T. Lindström, Hollviksnas, all of Sweden

[73] Assignee: Teltec Electronic Equipment AB, Lund, Sweden

[21] Appl. No.: 718,429

[22] Filed: Apr. 1, 1985

[30] Foreign Application Priority Data

Apr. 2, 1984 [SE] Sweden ................................ 8401789
Mar. 14, 1985 [SE] Sweden ................................ 8500608

[51] Int. Cl.$^4$ ............................................. A61B 10/00
[52] U.S. Cl. ......................................... 128/660; 128/663
[58] Field of Search ................................. 128/660-663

[56] References Cited

U.S. PATENT DOCUMENTS

| 4,101,961 | 7/1978 | Reiber ............................ 128/653 X |
| 4,357,944 | 11/1982 | Mauser et al. |
| 4,370,985 | 2/1983 | Takeichi et al. |
| 4,416,286 | 11/1983 | Iinuma et al. |
| 4,501,277 | 2/1985 | Hongo ............................ 128/660 |

FOREIGN PATENT DOCUMENTS 0042288 12/1981 European Pat. Off.
0127157 12/1984 European Pat. Off.

OTHER PUBLICATIONS

Hostetler, M. S. et al., "A Microprocessor-Controlled Echo Cardiographic Tracking System", IEEE BME Transactions, vol. BME-27, No. 5, May 1980.
"Real-Time Ultrasonography for Quantified Analysis of Fetal Breathing Movements", K. Marsal et al., The Lancet, Oct. 2, 1976, pp. 718-719.
"Device for Measurement of Fetal Breathing Movements", K. Lindstrom, et al.
"A Dual High-Resolution 2-Dimensional Ultrasound System for Measuring Target Movements", G. Gennser, et al.-Recent Advances in Ultra-Sound Diagnosis 3, pp. 71-75.
"A Phase-Locked Echo Tracking System for Recording Arterial Diameter Changes in Vivo", Hokanson, et al., J. Appl. Physiol 32(5) 728-733, 1972.
"Physiological Characteristics of Diameter Pulses in the Fetal Escending Aorta", Eriksen, et al., Acta Obstet Gynecol Scand 63: 355-363, 1984.

Primary Examiner—Kyle L. Howell
Assistant Examiner—Francis J. Jaworski
Attorney, Agent, or Firm—Cushman, Darby & Cushman

[57] ABSTRACT

The invention relates to apparatus which co-operate with an ultrasonic scanner. The apparatus includes a line dataprocessor which takes control of the activation of the ultrasonic crystals in the scanner head such that between each ultrasonic crystal activation for a viewing line on the image screen of the ultrasonic scanner a sequential activation takes place of two or three crystals or crystal groups each representing a respective measuring line. A marker is placed for each measuring line in a selected part-structure, such as a vessel, presented on the image screen, Echo-tracking dataprocessors seek the boundaries for the vessel along the measuring lines and lock onto these boundaries. A result dataprocessor computes continuously the changes in the vessel boundaries and calculates pulsewave diagrams for the vessel at the selected measuring lines and presents these diagrams on a presentation unit. The pulse-wave velocity in the vessel can be calculated on the basis of the resultant pulsewave diagrams, as can also the amplitude for the pressure pulse and the elasticity conditions in and around the vessel walls.

15 Claims, 10 Drawing Figures

APPARATUS FOR MEASURING PULSETILE PART-STRUCTURES WITHIN A LIVING BODY

FIELD OF THE INVENTION

The present invention relates to an apparatus for measuring movable part-structures within a living body, said apparatus being intended to co-operate with an ultrasonic scanner having an ultrasonic head provided with a plurality of ultrasonic transmitter units, and being arranged to generate pulsation diagrams representing movements of a pulsatile vessel in a living body. The invention pertains to the technical field of ultrasonic diagnostics, and relates more specifically to an apparatus which in co-operation with an ultrasonic scanner registers changes in distance between interfaces of different acoustic impedance with the aid of ultrasound reflected from the part-structure being measured, e.g. a blood vessel in a living body.

BACKGROUND OF THE INVENTION

It has long been known that stationary and mobile part-structures in a living body can be observed with the aid of different types of ultrasonic scanners. The invention can also be applied to advantage in co-operation with an ultrasonic scanner provided with a scanning head, also referred to as an ultrasonic transducer, comprising a linear array of ultrasonic transmitters, in which each ultrasonic transmitter can include one or more ultrasonic crystals and in which each of the transmitters is activated in sequence, one after the other, to emit an ultrasonic beam pulse, and a common ultrasonic receiver. A two-dimensional image of a deep section in a living body is obtained with such a scanner and shown on a screen. The moving image presented on the screen provides certain information concerning the mobility of the illustrated part structures of the body, but are required to provide a clearer representation of the actual movements.

In an article "A Dual High-Resolution 2-Dimensional Ultrasond System for Measuring Target Movements" by G. Gennser, K. Lindström, P. Dahl, M. Benthin et al in RECENT ADVANCES IN ULTRASOUND DIAGONIS 3, PROCEEDINGS OF THE 4TH EUROPEAN CONGRESS IN ULTRASONICS IN MEDICINE, Dubrovnik May 1981, there is described how it is possible with the aid of an ultrasonic head having linearly placed multiple ultrasonic transmitters to measure continually the momentary inner dimensions between two defining surfaces of a mobile, e.g. pulsating structure, in a living body, such as the aorta of human foetus. By taking these measurements at close time intervals, i.e. between each indication of a horizontal line, there is obtained a dimensional change at many points in time during the duration of one pulsation, and a pulsation diagram of pulsewave diagram can be drawn for a section through a pulsatile vessel or vein. In the penultimate paragraph on page 73 of the aforesaid article it is said that there are two markers although it should be noted here that the two markers are placed at two locations on the same horizontal line as that used as measuring lines, so that two markers here correspond to one of the elongated markers described hereinafter in the description.

The method described in this article has been found extremely valuable for providing visual pictures of movements, particularly of pulsating part structures in a living body, such as a blood vessel. The article, however, is only informative in respect of movement in one direction, i.e. the change in diameter as a function of time right through a part structure. This information gives only a limited picture of the state of the mobile part structure being measured, since the part structure, particularly when it is a blood vessel, partly leads a pulse wave in a direction transversely to that in which the change in diameter is indicated, and partly may undergo changes in this transverse direction which renders the pulsation diagram obtained in accordance with the known method highly dependent on which part structure the measurements are carried out. This circumstance is particularly applicable to arteries, especially in respect of older people where various types of constriction can be found relatively frequently. Consequently, there is a need of indicating changes in more than one dimension of movable structures.

SUMMARY OF THE INVENTION

The aforementioned problem is solved in accordance with the invention with the aid of an apparatus of a kind mentioned introductory having a control means which is operative to activate sequentially the ultrasonic transmitter units in an ordered sequence normal to the ultrasonic scanner and which between each activation of one of the ultrasonic transmitter units for use of the ultrasonic scanner is arranged to activate in sequence at least two selected measuring lines each of which represents a respective ultrasonic transmitter unit; a vessel wall indicating means arranged to receive the signal obtained in response to activation of the said selected ultrasonic transmitter units and which is arranged for each measuring line with each scan thereof to search two vessel boundaries and to calculate the change in said boundaries in relation to a preceding indication of the measuring line; and a computing means which calculates a pulsation diagram for each measuring line selected for the pulsatile vessel from the information obtained from the vessel wall indicating means and presents the pulsation diagrams on a presentation unit.

According to a feature of the invention the vessel wall indicating means includes two units, of which one is arranged to search for all measuring line scans at the boundary nearest to the measuring head for the examined vessel, and the other is arranged to search for all measuring line scans at the boundary located furthest away from the measuring head.

According to another feature of the invention the vessel wall indicating means is arranged to operate under two conditions, a setting or adjusting condition under which seeking of signal parts in echo signals registered in the ultrasonic head from each measuring line representing the vessel walls is arranged to take place and pulsation-diagram data is not processed, and a working condition under which for each measuring line indication shifting of signal components in the echo signal representing the vessel walls is arranged to be calculated and serves as a basis for computation of the pulsation diagrams by the computing means.

In accordance with one further development of the invention the apparatus according to the invention is suitable for measuring the pulse-wave rate in vessels. The differences between curve forms of pulsation diagrams representing different locations of a blood vessel may also provide information concerning the nature of the injury to the vessel. It is thus possible to obtain information relating to totally novel physiological parameters, such as segmental pulse-wave rate, and therewith regional elasticity properties of the vascular system.

In conventional ultrasonic equipment intended for measuring pulse-wave velocities in blood vessels, this equipment at present employing a Doppler-based method, the ultrasonic head must be positioned extremely precisely if a reproduceable and unchangeable measuring result is to be obtained. Measuring operations based on this technique also take as their starting point a mean diameter of the vessel in question, which gives rise to certain errors. In contrast hereto, it is possible when using apparatus according to the invention to readily detect a variation in the pulse-wave velocity, such variations being liable to occur in one and the same person at various points in time, owing to the fact that the apparatus according to the invention is relatively insensitive to whether the ultrasonic head has been placed in precisely the correct position or not, particularly when the selected measuring locations are relatively far apart. This renders the apparatus according to the invention suitable for examining periodically large groups of the population.

The automatic locking of the measuring area to a given part structure in the deep section presented on the screen associated with the ultrasonic scanner, in accordance with the invention, provides an instrument which can be readily managed. It would be extremely difficult, if not practically impossible, for an operator to line up the measuring areas for two or more measuring locations without the aid of this apparatus. Previously, this locking of the measuring area has been effected separately in different interfaces, instead of locking to a part structure of a specific nature and permitting the automatics to seek the interfaces of the part structure, as with the present invention.

Since data concerning pulse waves in the arteries contains a wealth of information relating to the cardio-vascular function, non-invasive measurement of these pulses is of particular interest in respect of human foetus, on which measurements cannot, of course, be made directly. The invention is not, however, restricted to measurements on human foetus, but can be applied to great advantage, for example, for taking measurements on the carotid artery of adult people, in order to detect characteristics at an early stage.

BRIEF DESCRIPTION OF THE DRAWINGS

The invention will now be described in more detail with reference to the accompanying drawings, in which.

DESCRIPTION OF THE PREFERRED EMBODIMENTS

Figure 1:
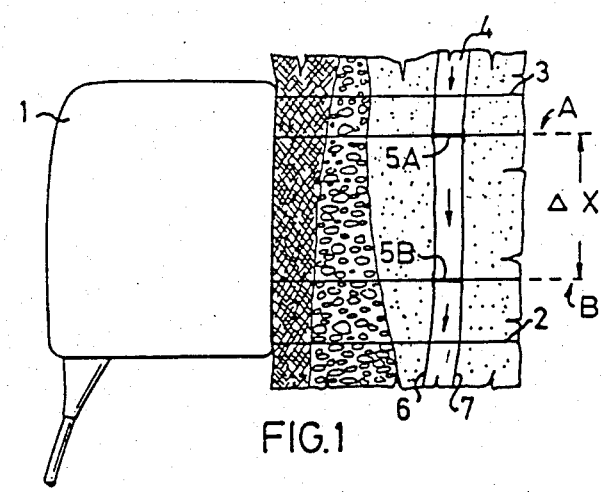
FIG. 1 illustrates an ultrasonic head attached to the skin of a body, of which a part is shown in cross-section down to a given depth.

FIG. 1 is a schematic illustration given to illustrate how the invention appears to the operator having charge of an ultrasonic scanner provided with apparatus according to the invention. An ultrasonic scanning head 1, which is suitably of the kind provided with a linear array of ultrasonic transmitters and a common ultrasonic receiver, is placed in abutment with the skin of a living body, which is shown in section in the figure to the depth to which the ultrasonic scanner is set for two-dimensional indication of the structure in the body. Sections to this depth can be selected with the majority of ultrasonic scanners. The ultrasonic head 1 has, for example, 64 transmitters, each of which can include one or more ultrasonic crystals. Thus, it is possible to record on an image screen 64 so-called viewing lines for the structure in a deep section of the body beneath the head 1. The image reproduced on the screen has substantially the same appearance as the illustrated section through the body in FIG. 1.

Figure 2A:
FIGS. 2A, 2B and 2C illustrates the sequence in which the automatic locking is effected.
Figure 2B:
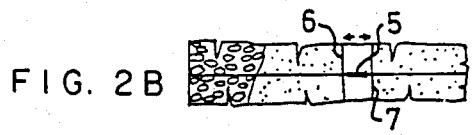
Figure 2C:
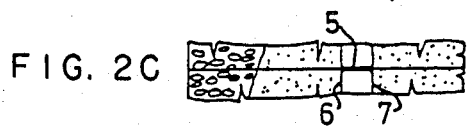
Figure 3:
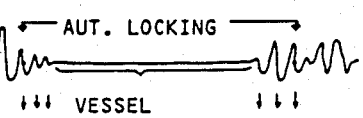
FIG. 3 is a signal image illustrating where locking takes place in the signal.

In FIG. 1 four viewing lines are marked, namely the two outermost lines 2,3 and two lines A and B located therebetween. With the aid of an ultrasonic scanner provided with apparatus according to the invention it is possible for the operator to select a given part structure in the structure illustrated on the screen, such as a blood vessel 4 for example; set a narrow marker 5, as illustrated in FIG. 2a, on a selected site in this part structure 4; and mark the measuring lines A and B to be used, whereafter the apparatus according to the invention automatically elongating each marker on respective measuring lines by scanning outwardly in both directions along the measuring line from the depth at which the marker is placed. FIG. 2b illustrates the marker 5 during the actual adjustment sequence, and FIG. 2c illustrates the marker 5 when the marker has locked to the interfaces 6,7 in the section, these interfaces representing the wall of the vessel. As an alternative to the operator selecting suitable measuring lines, the apparatus may be constructed to select automatically measuring lines having a set distance therebetween, wherewith the marker on the second line also follows the first. FIG. 3 illustrates an enlarged signal image of that part of the signal in the ultrasonic receiver on which the setting of the marker width has been produced. As will be seen, there is obtained a relatively uniform signal image along a measuring line from a homogenous region, which in FIG. 3 represents the interior of a vessel. The signal image has multi-periodic oscillation, however, at junctions at cell walls between the homogenous regions. Since it is usual for disturbance signal-portions also to occur within the homogenous region, the marker does not lock directly when meeting an oscillating signal-part, but locks on a zero-crossing subsequent to the passage of a pre-determined number of periods, this number suitably being three. In FIG. 3 zero-crossings at the rear flanks of a plurality of periods in the signal image adjacent the region representing the vessel have been marked with arrows, and locking takes place here at the third zero-crossing on each side of the vessel area. It will be understood that the forward flank can be chosen instead of the rear flank.

FIG. 1 shows that the operator can place at least two markers 5A and 5B on selected sites in a blood vessel. The advantage afforded hereby will be made apparent hereinafter.

Figure 4:
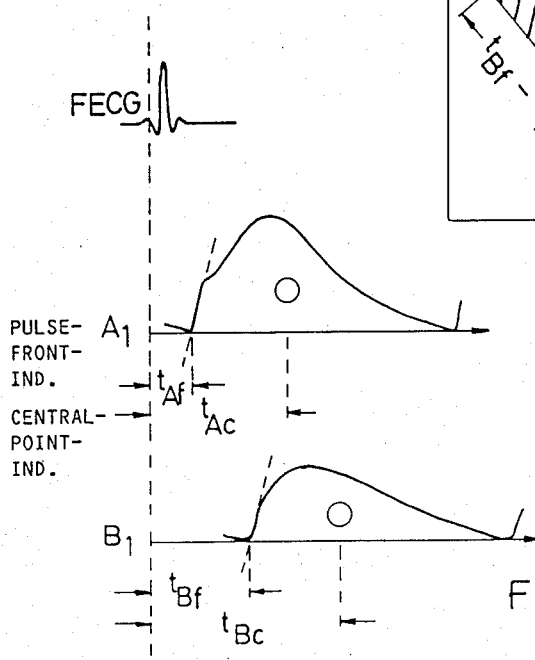
FIG. 4 illustrates two pulsation curves recorded with the apparatus according to the invention and illustrating two methods of determining the displacement in time between said curves.

FIG. 4 illustrates a pulsation diagram obtained for two markers 5A and 5B. These are presented to the operator on a separate screen, such as an oscilloscope screen for example, or can be drawn continuously by a pen recorder.

Figure 5:
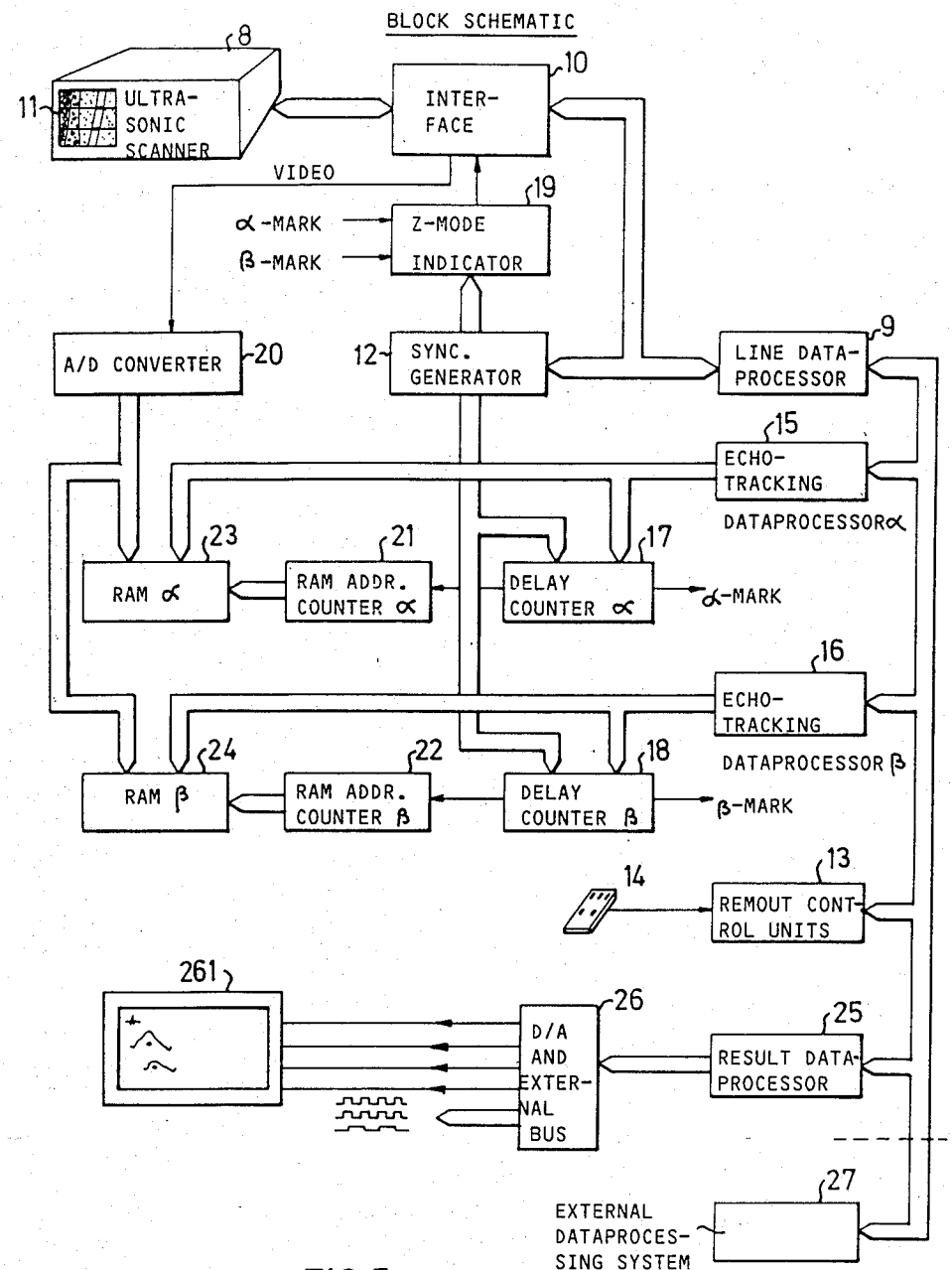
FIG. 5 is a block schematic of one embodiment of the apparatus according to the invention.

FIG. 5 is a block schematic of an embodiment of apparatus according to the invention in co-operation with a commercially available, two-dimensional ultrasonic scanner 8 having a linear-type ultrasonic head, also called a transducer. The ultrasonic scanner operates in real time and in B-mode.

A real-time scanner presents an image of the examined subject by transmitting ultrasonic pulses in the subject via the transducer. These pulses are reflected in the subject and detected. The detected echoes are presented on an image screen 11, therewith to show a two-dimensional image.

The transducer of the illustrated embodiment is a linear transducer having a large number of crystals lying along a line. The two-dimensional image is obtained by triggering these crystals, either one at a time in sequence or in specific groups in sequence with the line scans displaced in relation to one another. When the apparatus according to the invention is set into operation there is produced a veiwing image and the crystals or the groups of crystals corresponding to the selected measuring lines are triggered. In accordance with the invention, the internal control of horizontal lines, so-called viewing lines, is herewith set out of function. A line data processor line is instead connected to the ultrasonic scanner 8 via suitable interfaces 10 for the purpose of controlling the horizontal lines. The line dataprocessor 9 keeps a check on the measuring sequence and on which horizontal line or viewing line is to be shown at that moment on the screen 11. The dataprocessor also ensures that the markers 5A and 5B (see FIG. 1) show where the measuring line A and the measuring line B are located in the subject. The markers can be moved by the operator prior to commencing the measuring operation with the aid of a remote control unit 13 having a manual adjustment or setting device 14.

In order to obtain the highest possible resolution of the pulsation diagram, it is suitable to scan the measuring lines, i.e. the viewing lines, where the markers 5A and 5B are located between each indication of a new viewing line, although without showing the measuring lines on the screen 11 each time the lines are scanned. When the apparatus according to the invention is set into operation, the ultrasonic picture shown on the screen 11 will thus flicker to a slightly greater extent, owing to the fact that the image frequency is lower, i.e. a third of what is normal when two markers are selected, although this has not been found in practice to seriously impair the image quality. The viewing line sequences are thus line 0, A, B, line 1, A, B, line 2, A, B, ... line 63, A, B, line 0, A, B etc. The viewing image may instead be constructed by jump scanning, wherewith the scanning sequence is line 0, A, B, line 2, A, B, ... line 62, A, B, line 1,. A, B, line 3, A, B ... line 63, A, B, etc.

It will be understood that more than two lines may be provided with markers 5, although the more lines provided with markers the lower the image frequency on the screen 11 and the lower the maximum part-structure speed which can be tracked.

A synchronous generator 12 provides time control from the line dataprocessor 9 to other units in the circuit which require indication at the commencement of each line scan, such as scanning of a viewing line and measuring line.

The operator is able to adjust the measuring lines A and B to desired sites on the subject with the aid of the remote control unit 13 to which the manual control device 14 is connected, and the lines used as measuring lines are illustrated on the screen 11 with two markers. The line dataprocessor 9 ensures that these markers are shown in the correct positions on the screen. The line dataprocessor also ensures that "echo-tracking dataprocessors" 15,16 are informed of which meausuring line is sent at that moment.

At the beginning of a measuring sequence the operator informs the echo tracking dataprocessors 15 and 16 from which point on the screen a further scanning of the echoes is to take place, i.e. subsequent to the operator having placed the initially punctiform markers 5A and 5B at a desired depth, e.g. at some central location in a blood vessel. Subsequent to pressing the "search" key or button on the device 14, a plurality of measuring sequences take place, in which each time the measuring lines are scanned the echo-tracking dataprocessors 15 and 16 detect whether or not a signal part representing a vessel wall is located at the marker, and moves the marker outwardly when no such signal part is present. The echo-tracking $\alpha$ dataprocessor 15 senses the vessel wall lying nearest the ultrasonic head for both the measuring line A and the measuring line B, and the echo-tracking $\alpha$ dataprocessor 16 senses the part of the vessel wall lying at the greatest depth for both the measuring line A and the measuring line B, i.e. the $\beta$ dataprocessor seeks outwardly and the dataprocessor seeks inwardly in the structure. No calculation of pulsation-diagram data takes place during this setting seeking sequence.

The punctiform markers 5A and 5B are spread out during the seeking sequence over some measuring sequences, until the echo-tracking dataprocessors when analysing the signals derived from the mesausring lines meet signal parts which represent vessel walls, where they lock at preferably the third zero-crossing. By providing two echo-tracking dataprocessors 15, 16, of which the one locks against the forward vessel wall for both the measuring lines A and B and the other locks against the rear vessel wall, it is possible to select more than two markers on the same part structure, without requiring the hardware to be especially adapted to this selection. If, on the other hand, movements of a larger number of movable part-structures in the examined structure are to be investigated simultaneously, such as two blood vessels located one beneath the other for example, two echo-tracking dataprocessors are required for each such part-structure. Each echo-tracking dataprocessor 15 and 16 co-acts with a respective counter 17 and 18, a respective RAM-address counter 21 and 22, and a respective random access memory store 23 and 24, hereinafter referred to as a RAM-store.

Figure 6:
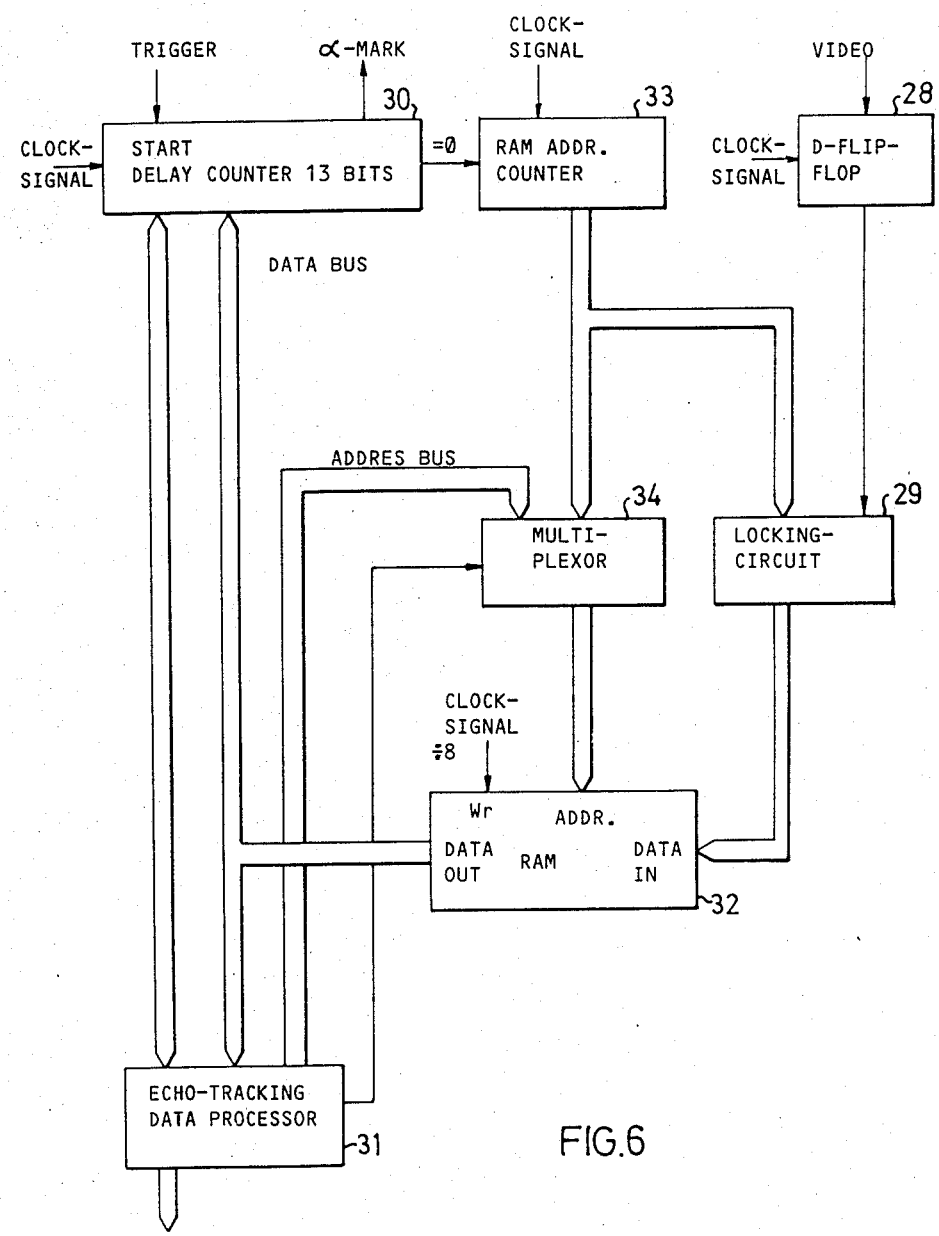
FIG. 6 is a block schematic of an alternative embodiment of a part of the apparatus illustrated in FIG. 5.

FIG. 6 illustrates an embodiment different to that of FIG. 5 of the particular coupling modes between delay counter, RAM-address counter, RAM-store, together with circuits for indicating what is to be written into the RAM-store.

In the FIG. 5 embodiment the echo-tracking dataprocessors 15 and 16 thus learn from the remote control unit 13 at the beginning of a measuring operation from which point on the screen 11 new search of the echoes is to take place, whereafter the dataprocessors receive continuously from their respective RAM-stores updated values of the position of the echoes from the part-structures which form the basis of decision and tracking. For each echo-tracking dataprocessor with peripheral equipment the echo-tracking dataprocessor 15, 16 stores the values of a new search for both the lines A and B in the delay counter 17,18, which is counted down to zero from the time of the transmission of an ultrasonic pulse for a measuring line, this count-down occurring at the instance of the new search. When reaching zero the respective delay counter 17 and 18 delivers a pulse whose position on the intended line is indicated to the ultrasonic scanner through a signal applied to an input on a Z-mode indicator 19 coupled to the interface 10, and activates the respective RAM-address counter 21 and 22. In the FIG. 5 embodiment the video signal converted by the analogue/digital converter 20 is written into the RAM-store 23 and 24, respectively. Each RAM-address counter 21 and 22 is limited to solely count upwardly a pre-limited number of addresses subsequent to activation from its associated delay counter 17 and 18 respectively, wherewith only a limited part of the analogue/digital converted video signal is written into the associated respective RAM-store 23 and 24, subsequent to the Z-mode indicator 19 having obtained the indication α-marking or β-marking on one of its inputs.

When the signal is written into respective RAM-stores 23 and 24 in real time, the echo-tracking dataprocessors can then analyse directly, i.e. in quasi-real time, the position of the echoes in order to calculate how far they have moved from the position in which they were located at nearest preceding transmission of the same line. This value is transferred to a result dataprocessor 25, which then carries out calculations on the movements, of the part-structure which are partly fed to a unit 26 which effects digital/analogue conversion of the signal, for recording the same on a pen recorder or to show the signal visually on an analogue image screen. The unit 26 may also transfer the digital signal obtained from the result dataprocessor 25 to an external bus so that it can be transferred to some external unit for further processing. It is also possible to connect-up an external dataprocessing system 27 in addition to or instead of the result dataprocessor 25, with which dataprocessing system storage in a mass memory-store can be made for later analysis of the measuring values obtained. When solely an external dataprocessing system is connected-up and the result dataprocessor is not present in the system, each echo-tracking dataprocessor 15 and 16 may be programmed to calculate the shifts in the vessel wall for the purpose of activating a respective associated delay counter 17 and 18 at an intended location on the next following measuring line.

FIG. 6 illustrates an alternative embodiment of those parts of the circuit in FIG. 5 which include the elements 15, 17, 20, 21, 23 or 16, 18, 20, 22, 24. Since the operator is actually only interested in the zero-crossings on the videosignal, as evident from FIG. 3, this fact can be utilized for signal processing purposes. The videosignal, i.e. the undetected ultrasonic signal, is supplied to the input of a D-type bistable flip-flop 28, to the clock input of which clock pulses of suitable clock frequency, for example 70 MHz., are applied. The videosignal with the direct-current voltage component filtered out varies around the zero-line. The flip-flop 28 receives a "1"-signal on its input as soon as the videosignal is positive, and an "0"-signal when the videosignal is zero or negative. The signal on the input line is clocked to the output with the clock signal and is supplied to a control input on a locking circuit 29 which, when the signal from the flip-flop 28 changes from a "1"-signal to an "0"-signal, applies the signal in the RAM-counter to a signal input on the locking circuit and holds the value of this signal until the signal obtained from the flip-flop 28 again changes from "1" to "0". The signal on the output of the locking circuit 29 is the signal stored at that moment in the locking circuit, this signal later being stored in the RAM-store 32 with some suitable written clock signal e.g. 70/8 MHz.

As in the circuit illustrated in FIG. 5, the delay counter 30 obtains a triggering or initiation signal from the echo-tracking dataprocessor and counts down to zero from a value obtained in the counter 30 from the echo-tracking dataprocessor 31, this value being updated for each measuring operation. When the delay counter has counted down to zero, the counter supplies a pulse to a trigger input of the RAM-address counter 33, which begins to count upwards at the same clock frequency as the clock frequency of the D-flip-flop 28.

The output signal of the RAM-address counter 33 can be said to represent continuously the time from the new-searching point, i.e. the point in time at which the echo-tracking dataprocessor has counted down to zero. This point at which the new search takes place is chosen to lie at a suitable time point prior to that time point at which the position of the vessel wall was established during the previous scanning of the same measuring lines. The output of the counter 33 is connected to the signal input of the locking circuit 29, the information stored sequentially in the locking circuit 29 thus representing the times of the video-signal zero-crossing that point in time that a new search was commenced.

The output of the RAM-address counter 33, in addition to the lines having the three least significant bits, is also connected to the one output of a multiplexor 34, to the other input of which there is applied the address bus of the echo-tracking dataprocessor. When reading into the RAM-store, the multiplexor 34 transfers the output of the counter 33 to the address input of the RAM-store 32, when reading the address bus. The echo-tracking dataprocessor 31 guides the multiplexor 34 on its DS-input (DS=Data Select) to select which of these inputs shall be connected to its output at each instance. The RAM-store 32 is clock-controlled at a clock frequency which equals the clock signal to the RAM-address counter with several element divided by a factor evenly divisible by 2, such as 8, the clock frequency for the store 32 being, for example, 70/8 MHz. The video-signal is thus synchronized with the higher pulse frequency of, for example, 70 MHz in the D-flip-flop 28 and the negative zero-crossings lock the RAM-address value in the locking circuit 29, and each locked value is read into the RAM-store with the lower clock frequency of 70/8 MHz.

Thus, in this case, it is not the actual ultrasonic signal which is read into the memory store, but the time positions of the negative zero-crossing in relation to the new searching point transferred previously in the delay counter. The zero-crossing onto which the system locks can be caused to be written into a given cell in the RAM-store, by continually changing the new search time point. When the zero-crossing, i.e. the part-structure, moves, the value in this RAM-cell will change. This change in value becomes a measurement of the extent of such movement and it is with this change in value that the value in the delay counter is changed between each scan of the measuring line in question. The value in the delay counter is fed to the result dataprocessor 25 for each processing operation. Signal processing is then effected freely between each ultrasonic measuring pulse.

Each RAM-store 32 thus has one such RAM-cell, and two RAM-stores are provided for each part-structure, such as the aforesaid blood vessel, upon which measurements are to be made. Up to four measuring lines can be selected before flickering of the image presented on the screen 11 becomes too disturbing, unless a scan converter technique is employed, although the best result is nevertheless obtained when the number of measuring lines is restricted to two.

From the values obtained from the echo-tracking dataprocessors the result dataprocessor 25 (see FIG. 5) calculates continuously, i.e. for each measuring sequence, the distances between the simultaneous measurements taken on two mutually opposing walls in the measured part-structure, and the result of these calculations is fed to the indicating unit 261. Cardio-sound from the patient under examination can also optionally be taken up and supplied to the result dataprocessor and recorded simultaneously on the screen 261, to provide a time reference. (Not specifically illustrated signalwise in FIG. 5.) Prior to recording the signal on the screen 261 the direct-current component is automatically subtracted from the signal, so as to be able to amplify the signal to such an extent that the variation range of the signal can be illustrated as clearly as possible.

As illustrated in FIG. 4, the two curves $A_1$ and $B_1$ representing the two markings A and B are displaced relative to one another in time. This displacement in time is caused by movement of the blood pressure pulse along the blood vessel at a certain velocity c, and this velocity can thus be obtained as the relationship between the distance $\Delta x$ between the measuring lines divided by the time displacement $\Delta t$ between the curves A and B, i.e. $c = \Delta x / \Delta t$.

Owing to the fact that the vessel on which measurements are taken is not completely homogenous along its length, which is quite common, particularly in the case of the older people, the curves $A_1$ and $B_1$ may have substantially different forms, which in other respects provides important medicinal information concerning various types of change in the vessel walls. However, as a result hereof one is liable to encounter difficulties in defining the time displacement between the curves $A_1$ and $B_1$ which is to be used for calculating the pulse wave velocity c. FIG. 4 illustrates two different possibilities of determining this time difference.

The simplest method of determining the said time difference from a technical aspect is to determine the time difference between the fronts of the two pulsation curves $A_1$ and $B_1$. The degree of accuracy to which such measurement can be made, however, is reduced by any occurring noise interference, when measuring is effected solely at a particular point on the curves.

A more satisfactory method is to shift a replica of the first pulse waveform along the time axis and locate the position at which the integrated, squared differences between the displaced waveform or curve and the second pulsation curve plus noise is minimized. This is equivalent to comparing simultaneously all points in the two waveforms, in order to find a solution which provides the best fit.

Both of the aforementioned methods provide the time difference $t_{Bf} - t_{Af}$ in FIG. 4.

Additional problems are created, however, by the fact that, as beforementioned, the pulse wave often changes considerably in shape, as it propagates along the vessel being examined. There may be various reasons for this, of which the most important are:

(a) a velocity dispersion, i.e. various frequency components of the pulse wave travel at different speeds;
(b) frequency dependent attenuation of the propagating pulse waves;
(c) non-linear elastic behaviour of the vessels with increasing distension;
(d) the effects of increasing elastic rigidity of arteries with increasing distance from the heat together with the narrowing of the vessels as they branch; and
(e) the base vascular tone can vary during the recording time.

This renders the task of accurately estimating the time difference between two pulse waves difficult. The problem is similar to that encountered when using indicators or labelling devices, such as dye, radioisotopes, heat and saline solutions within the field of medical physiological assays. When a mass of indicating substance passes through a system, the multitude of particles contained in the mass become spread with respect to the distance from the supply locations along the vascular system, and therefore are also spread with respect to their time of arrival at the measuring location. In cases such as these the obtained signal is subjected to a type of "centroid" calculation. The same calculating principle can be used for the two curve forms $A_1$ and $B_1$ to calculate the mean traverse time (MTT) of pulse waves in accordance with the formula $$t_c = \frac{\int_T t \cdot c(t) \cdot dt}{\int_T c(t) \cdot dt}$$

where c(t) is the radial dilation of a vessel as a function of time. This results in a calculation which makes use of all parts of the pulse waveform and thus can be automatically calculated and with limited sensitivity to noise. $t_{Ac}$ and $t_{Bc}$ in FIG. 4 are obtained with this method.

The strong interaction on the wave form of the pulse wave from the elastic properties of the vessel and surrounding tissue should not merely be considered a disadvantage. On the contrary, much useful information concerning normal and pathological conditions can be derived from an accurate analysis of differencies between the recorded pulse forms $A_1$ and $B_1$. As an example it can be mentioned that:

(a) the velocity dispersion has been considered theoretically and experimentally in hydraulic models, where it was found to be due to the viscosity of the liquid within the tube and to the viscous component in the visco-elastic walls.
(b) the apparent broadening of the pulse-wave form in its travel along the vessel is often not due to velocity dispersion but rather to the result of differential attenuation of the frequency components of the pulse wave. If we assume that the pulsewave equation has the standard form $A = A_O \exp.(-k \cdot x)$ the attenuation coefficient K is show to be frequency dependent.

This often increases linearly with the frequency, i.e. $K=\alpha \cdot f$, where $\alpha$ is constant and f is the frequency. Estimation of $\alpha$ might become an important parameter for quantitative differentiation between normal and pathological vascular tissue.

(e) the pulse-wave velocity is dependent on the blood pressure. There is evidence that the wave velocity of excised arterial segments increases proportional with the diastolic pressure. Non-invasive pressure-monitoring can be effected continuously in accordance with the invention with the aid of the time difference of the curves $A_1$ and $B_1$ and by comparison of their curves forms. Thus, blood pressure can be measured non-invasively by utilizing the modified derivation (according to Bramwell & Hill) of the pulse-wave velocity $c=kV\cdot \Delta p/\Delta V$, which can be transformed to $\Delta p = \kappa_2/c^2 \cdot v\Delta V$, where $\Delta p$ is the absolute value of the pulse pressure, i.e. the difference between systolic and diastolic blood pressure, K is a constant, V is volume and $\Delta V$ is volume change. The result dataprocessor 25 carries out this calculation on the obtained curve forms $A_1$ and $B_1$ and feeds the result of this calculation to an external unit, via the external bus from the unit 26.

The calculated pulse-wave velocity c can also be used to calculate the vessel elasticity, by using Moens formula $$c = K_1 \cdot \frac{g \cdot E \cdot a}{D \cdot d}$$

where E is the detected vessel elasticity, a is the thickness of the vessel wall, D is the density of the blood, d is the cavity diameter of the vessel in the diastole state and $K_1$ and g are constants. The result dataprocessor 25 calculates d from the difference between the values of outer and inner vessel wall positions respectively at a time point with minimum value in the pulse diagram, such as $t_{Ac}$ and $t_{Bc}$ in FIG. 4, for one of the measuring lines A or B, these values being stored in the RAM-store 23 and the RAM-store 24 (FIG. 5). The elasticity E of the vessel is then calculated with the aid of the formula $$E = \frac{c^2 \cdot D \cdot d}{K_1^2 \cdot g \cdot a}$$

transformed from the above formula.

Figure 7:
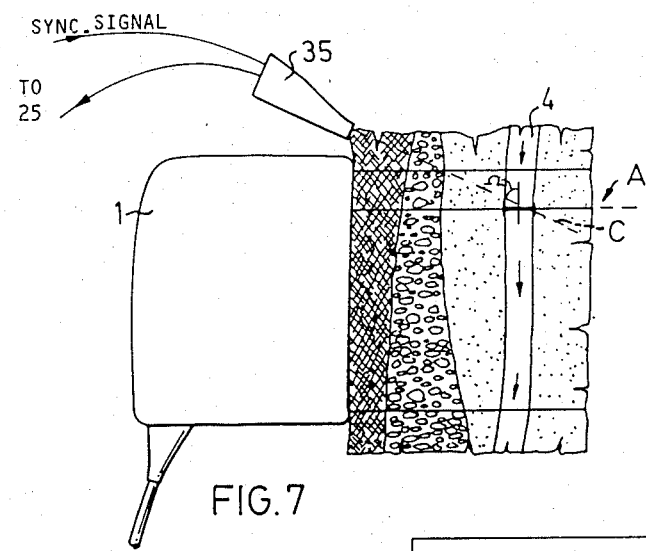
FIG. 7 illustrates schematically an embodiment which co-operates with a Doppler-ultrasonic measuring apparatus.

As mentioned in the introduction, Doppler-ultrasonic measuring processes are often used for flow measuring purposes. In this respect, the method takes as its starting point a mean diameter of the vessel in question, which gives rise to certain errors. As illustrated in FIG. 7, a Doppler-ultrasonic meter 35 can be placed adjacent the ultrasonic scanning head 1, and inclined at an angle $\Omega$ so that its transmitted signal passes along the line C towards the same part of the blood vessel 4 as the one measuring line A. The signal deriving from the meter 35 can be fed to the result dataprocessor 25 in FIG. 6 (not shown). A reduction in error experienced wit the Doppler-measuring process can be obtained by employing the Doppler-process concomittently with a vessel-diameter measuring process. In this case, the Doppler-ultrasonic meter 35 is triggered to activation with a synchronizing signal at the same time as a measuring line is scanned, on that the meter 35 is activated for measuring instead of the measuring line B directly subsequent to scanning the measuring line A. The measuring signal obtained in the meter is passed to the result dataprocessor 25, which also obtains information relating to the diameter of the vessel at that time. The result dataprocessor 25 calculates the rate f flow at that point in time with the aid of these two items of information and calculates the mean value of the flow over a pulse period, and with the aid of a stored $\Delta p$ of the pulse pressure is also able to calculate the vessel tone at that moment in time with the aid of the formula $$R_{vessel} = \Delta p / \text{FLOWRATE}$$

where $R_{vessel}$ is vessel tonus, $\Delta p$ is the pulse pressure and FLOWRATE is the calculated rate of flow.

As with the aforegoing, the ultrasonic scanner 8 constantly presents a fresh "real-time" image of the measuring environment in question, which is of necessity required for ultrasonic easuring equipment to be used in clinical work. The marking line A is particularly shown on the screen 11, so that the operator is able to see immediately where the vessel diameter measurement takes place. The sample volume used for the Doppler-ultrasonic measurement of the blood flow with the meter 35, which is effected with a so-called pulsated doppler, is shown on a separate indicator (not shown).

Unfortunately certain limitations are found, due to the laws of nature.

(1) The time taken to send an ultrasonic pulse to the depth R in the body and obtain an echo is $t=(2*R)/c$, where c is the ultrasonic velocity in the tissue in question, normally 1540 m/s. If the next pulse is sent immediatley the preceding pulse has returned from R, the maximum pulse repetition frequency becomes $p=1/t$ or $c/(2*R)$. In order to obtain a practical value assume that $R=10$ cm, then p becomes $1540/(2*0.1)=7700$ pulses/s (this is simplified, since the Doppler-pulse must travel a longer distance). These ultrasonic pulses shall suffice for both image generation and measurement of cell diameter and blood flow. Consequently there is applied the previously described cyclic sequence of the transmission pulses, i.e. (1) for vessel measurement, (3) for doppler, (4) for image, etc.

There is then obtained about $7700/3 \approx 2570$ pulses/s for each area of use. In respect to images, 10 images/s are conceivable, each comprising 257 horizontal lines. This is probably fully acceptable particularly in view of the fact that in practice the image can be held quite still, i.e. flicker-free, by using a quick refresh image memory.

(2) Vessel measurements can be made 2370 times/s. Conflict is to be found here. Normally it is desired to use the highest possible ultrasonic frequency in order to obtain good spatial resolution, i.e. sharp lines in the ultrasonic image. However, this limits the maximum tracking speed of the phase locking system. In practice, however, it is possible to obtain a sufficiently high tracking speed for vessel pulsations by using 3-7 MHz ultra-sound.

(3) Doppler: It is known that pulsated ultrasonic doppler has a limited so-called range velocity: $v*R=c^2/(8*f)$, where v is the maximum radial velocity, R is distance, and f is the ultrasonic frequency used. When $f=5$ MHz and $R=0.1$ m, $v=(1540)^2/(0.1*8*5*10^6) \approx 0.6$ m/s.

This does not suffice for clinical use. In this case it is possible to use the trick to lower and to use the ultrasonic frequency for the ultrasonic doppler for instance to 1 MHz, raising v to 3 m/s (desired value at least 1.5-2 m/s). Finally the limit for the measurement of the blood flow-rate can be further increased by increasing the angle Ω between ultrasonic transducer and blood vessel from a normal of 45° up to about 60° (if the angle is made larger than this the signal-noise ratio will be drastically impaired, and will make measuring impossible at 90°).

The problem with this lowering of the ultrasonic frequency, however, is that the resultant ultrasonic beam becomes much too broad and non-specific. Practical tests have shown, however, that there can be obtained with the aid of a focused transducer or emitter a beam width in the range in question which is equally as good as or better than a conventional non-focused emitter of higher frequency (5 MHz).

In the foregoing there has been described ways in which it is possible to produce simultaneously a limited number, such as two or three of pulsation diagrams, and also how the apparatus according to the invention with the aid of these diagrams is able to calculate the mean flow rate in an examined vessel between the selected measuring lines and also how the apparatus is able to calculate other properties of a vessel with the aid of the curve forms. In addition, it is possible to conclude certain properties of the examined vessel, for example as to whether there is a thickening in the vessel wall or the like within the area examined. In order to obtain the highest accuracy possible with the use of two measuring lines A and B, these lines should be placed relatively far apart, so that $\Delta x$ is large.

Those methods used at present in cell wall assays, for example examinations of the caroted artery, there is utilized, inter alia, the fact that local changes in a cell wall result locally in different pulse wave velocities, such that the pulse wave velocity is greater at a thickened portion than at a portion in which there is no thickening. As will be understood, an advantage is afforded when a changed portion of an examined artery can be localized directly, such a possibility being fully enabled by a further development of the invention.

If when examining a patient it is found that the two curve forms $A_1$ and $B_1$ in FIG. 4, are relatively the same, there are good grounds to suppose that the examined vessel has not undergone any particular change between the measuring locations. No additional examination need then be made.

Figure 8:
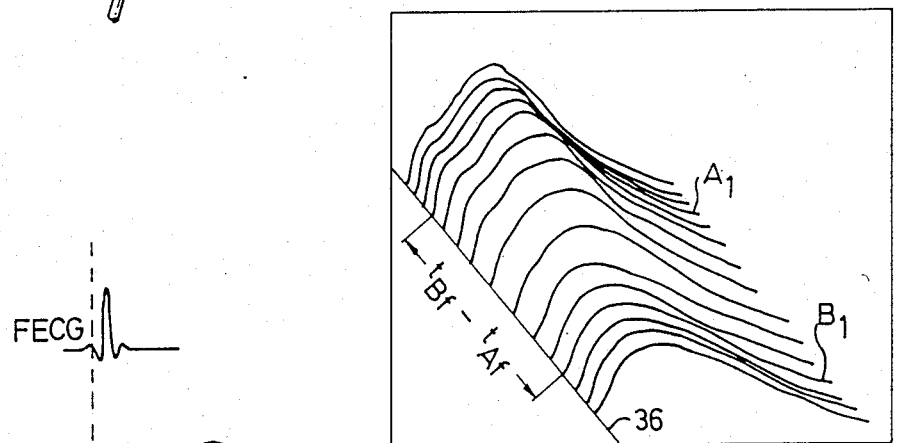
FIG. 8 is a relief diagram which can be produced with a further development of the apparatus according to the invention.

On the other hand, if there is a high degree of dissimilarity between the curve forms $A_1$ and $B_1$, for example such as the dissimilarities illustrated in FIG. 4, there may well be justification to examine the reasons herefor more closely. Accordingly, in accordance with a further development of the invention, the operator may re-set the apparatus through the device 14 so as to obtain a relief diagram of the type illustrated in FIG. 8 for that part of the vessel which lies beneath the transducer of the ultrasonic scanner. In FIG. 8 a plurality of pulsation diagrams are presented simultaneously on, for example, an image screen, so that they connect with a common time axis 36 which extends preferably obliquely on the screen and which in the case illustrated in FIG. 8 is placed after the front pulsation flanks but can, of course, be placed instead after the aforedescribed, calculated central point, or "centroid point" of the different curves. The sound from the patient's heart may be recorded for example, and used as a time reference.

As mentioned in the aforegoing a favourable effect is obtained with respect to the image on the screen of the ultrasonic scanner 8 and on the actual resolution of the pulsation curves when more than two or three measuring lines are used. Consequently, when the operator presses a key marked "relief diagram" on the device 14, the remote control unit 13 instructs the result dataprocessor 25 to order the line processor 9 to place two of three measuring lines relatively close together in that part of the image on the screen 11 in which the first viewing lines in an image are recorded. In a first measuring sequence a pulsation diagram is recorded for one or more pulsation periods in the aforedescribed manner. The thus obtained diagrams, which represent a period of the pulse stroke and with calculated mutual time displacement, are stored in a memory in the result dataprocessor. The diagrams can also be recorded at the same time on the image screen 22b. The result dataprocessor 25 then shifts measuring lines on the screen 11 to a following two or three viewing lines with the same spacing therebetween as the first measuring lines and with the same distance between the last measuring line in the first pulsation measuring sequence and the first measuring line in the second pulsation measuring sequence, records the pulsation diagrams with the same time reference as that for recording the first diagram in the first pulsation measuring sequence subsequent to adjusting the positions of the markers and storing these pulsation diagrams together with the diagrams in the first pulsation measuring sequence in a respective memory and also recording these diagrams on the screen 26l. The result dataprocessor 25 then again shifts measuring lines on the screen 11 etc., and continues to to record pulsation diagrams in different pulsation measuring sequences until measuring lines covering the whole of the screen 11 have been used. The pulsation diagrams recorded on the screen 261 are used progressively as the measuring process proceeds.

As beforementioned a conventional number of viewing lines for an ultrasonic image is 64. It is not necessary, however, to have such a large number of measuring lines, but that each third or each fourth viewing line can be chosen as a measuring line, thereby enabling the pulsation diagrams to be recorded relatively quickly. Since the separate pulsation diagrams forming a relief diagram are recorded in pairs or threes at a speed corresponding at most to half the period of the pulse of the examined person, the choice of the number of measuring lines selected is a question of balance between a desired line division of the relief diagram and the time taken to record the diagram as a whole. FIG. 8 illustrates in a slightly exaggerated fashion the appearance of a relief diagram when a constriction is located approximately centrally of the vessel area examined. Thus, the separate recorded pulsation diagrams at the centre of the constriction are less dense than at the sides of the constriction. The pulsation diagrams $A_1$ and $B_1$ in FIG. 4 are particularly shown in FIG. 8. In addition, the time difference $t_{Bf} - t_{Af}$ has been shown in order to illustrate the relationship between the pulsation curves in FIG. 8 and those in FIG. 4.

Many modifications can be made within the scope of the invention.

We claim:

1. Apparatus for measuring movable part structures within a living body, said apparatus being intended to co-operate with an ultrasonic scanner having an ultrasonic head provided with a plurality of ultrasonic transmitter units, and being arranged to generate pulsation diagrams representing movements of the movable part structures in a pulsatile vessel in the living body, comprising:

control means, operative to sequentially activate the ultrasonic transmitter units in an ordered sequence for, between each activation of one of the ultrasonic transmitter units, defining at least two selected measuring lines, each of which is associated with a respective associated ultrasonic transmitter unit and for scanning each said measuring line in a sequence using said associated transmitter unit and producing a signal indicative thereof;

vessel wall indicating means, arranged to receive the indicative signal obtained in response to the scanning using the selected ultrasonic transmitter units for scanning two vessel boundaries with each scan of each said measuring line to generate information used to calculate a change in condition of such boundaries in relation to a preceding indication of said measuring lines;

computing means for calculating a pulsation diagram for each said measuring line for the pulsatile vessel from the information obtained from the vessel wall indicating means; and presentation means for presenting the pulsation diagrams.

2. Apparatus according to claim 1, wherein the vessel wall indicating means includes two units, a first of which is arranged to search all measuring line scans at the boundary nearest to said ultrasonic head for the examined vessel, and a second of which is arranged to search all measuring line scans at the boundary located farthest away from said ultrasonic head, both of said first and said second unit searching for a change in condition of said boundary in relation to a previous indication.

3. Apparatus according to claim 2, wherein the vessel wall indicating means comprises means for operating under two conditions, (1) a setting or adjusting condition under which seeking of signal parts in echo signals registered in the ultrasonic head from each measuring line representing the vessel walls is arranged to take place, and under which pulsation-diagram data is not processed, and (2) a working condition under which for each measuring line indication, shifting of signal components in the echo signal representing the vessel walls is arranged to be calculated and is included in the information used for computation of the pulsation diagrams by the computing means.

4. Apparatus according to claim 2, wherein each unit includes echo-tracking means and volatile memory storage means, the echo-tracking means for, during each measuring sequence, marking a new search time point for each measuring line scan, in which a binary representation of the echo signal for the measuring line commences to be read into the volatile memory storage means, such time point being dependent upon information read into the volatile memory storage means in a preceding measuring sequence.

5. Apparatus according to claim 4, wherein said volatile memory storage means is for storing solely time points for flank, rear flank or front flank type zero crossings for the echo signal for each measuring line with a storage period which is substantially greater than the zero-crossing period; and for changing the new search time point based on the value contained in a given cell in the volatile memory storage means.

6. Apparatus according to claim 1, further comprising computing means for computing a time difference $\Delta t$ between the pulsation diagrams for a vessel which, in the examined body, crosses two measuring lines, said computing means being supplied with the distance $\Delta x$ between the ultrasonic transmitters for the selected measuring lines in the ultrasonic head, and which is also for computing the pulse wave velocity c in the examined body as $c = \Delta x / \Delta t$.

7. Apparatus according to claim 6, wherein said computing means computes the time difference $\Delta t$ as a time difference between the front flanks of the pulsation diagrams within a pulsation period.

8. Apparatus according to claim 6, wherein said computing means computes the time difference $\Delta t$ as the time difference between centroid calculations for each of the curve forms in the resultant pulsation diagrams.

9. Apparatus according to claim 6, wherein the computing means includes means for computing a pulse pressure $\Delta p$ in accordance with the formula:

$$\Delta p = \frac{c^2}{K^2} \frac{\Delta V}{V}$$

wherein V is volume, $\Delta V$ is the change in volume of the vessel, K is a constant and c is a pulse wave velocity.

10. Apparatus according to claim 9, further comprising memory means for storing the value p of the pulse pressure, and further comprising a Doppler-ultrasonic flow meter, which can be placed adjacent the ultrasonic head and aligned towards the blood vessel being examined;

and wherein the control means can be adjusted to scan in sequence, between each scanning by one of the ultrasonic transmitter units, a selected measuring line representing the ultrasonic transmitter units and the Doppler-ultrasonic flow meter;

and wherein the computing means is also for calculating the momentary vessel diameter on the basis of the measuring line scan and the flow, with guidance from the signal obtained from the Doppler-ultrasonic flow meter and said vessel diameter measurement; and in wherein a mean flow (FLOW) is calculated for one pulse period, a vessel tonus $R_{vessel}$ being calculated from the formula $$R_{vessel} = \Delta p / \text{FLOW}.$$

11. Apparatus according to claim 10, wherein the frequency of the Doppler-ultrasonic flow mefter is within the frequency region 0.5 to 1 MHz.

12. Apparatus according to claim 10, wherein the Doppler-ultrasonic flow meter is aranged to be placed in an alignment such that the angle ($\Omega$) between its alignment and the examined blood vessel is greater than 45° C. but not greater than 60°.

13. Apparatus according to claim 1, wherein the frequency of the ultrasonic scanner is chosen within the frequency region 3 to 7 MHz.

14. Apparatus according to claim 6, wherein the computing means is also for computing the vessel elasticity E in accordance with the formula $$E = \frac{c^2 \cdot D \cdot d}{K_1^2 \cdot g \cdot a}$$

where a is the thickness of the vessel wall, D is the blood density, d is the cavity diameter of the vessel in a diastole period and $K_1$ and g are constants.

15. Apparatus according to claim 1, wherein the computing means, includes means for automatically causing the control means for the ultrasonic transmitter units to effect in a sequential sequence, with each period in the sequence including at least one period of the pulsation in the examined vessel measurements on a limited number of measuring lines with positions on the screen selected by the computing means with a change in measuring lines for each period in said sequence, such that at the end of said sequential sequence, measurement has been effected along a plurality of measuring lines spaced at an equal distance apart; and wherein the computing means is also for computing pulsation diagrams for the vessel with each measuring line scan using a predetermined time reference and for presenting all pulsation diagrams simultaneously on the presentation unit as a relief diagram.

* * * * *